United States Patent
Takeda et al.

(10) Patent No.: US 8,115,177 B2
(45) Date of Patent: Feb. 14, 2012

(54) RADIATION DETECTION APPARATUS AND RADIATION IMAGING SYSTEM

(75) Inventors: Shinichi Takeda, Honjo (JP); Yoshihiro Ogawa, Hachioji (JP); Satoshi Okada, Zama (JP); Masato Inoue, Kumagaya (JP); Kazumi Nagano, Fujisawa (JP); Keiichi Nomura, Honjo (JP); Satoru Sawada, Kodama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 242 days.

(21) Appl. No.: 12/095,748

(22) PCT Filed: Jan. 19, 2007

(86) PCT No.: PCT/JP2007/051208
§ 371 (c)(1), (2), (4) Date: Jun. 2, 2008

(87) PCT Pub. No.: WO2007/086485
PCT Pub. Date: Aug. 2, 2007

(65) Prior Publication Data
US 2009/0283685 A1  Nov. 19, 2009

(30) Foreign Application Priority Data

Jan. 25, 2006 (JP) ................................ 2006-016396
Jan. 5, 2007 (JP) ................................ 2007-000512

(51) Int. Cl.
*G01T 1/20* (2006.01)
(52) U.S. Cl. ................................ 250/370.11
(58) Field of Classification Search ............... 250/370.11
See application file for complete search history.

(56) References Cited

U.S. PATENT DOCUMENTS

| | | | |
|---|---|---|---|
| 4,980,553 A * | 12/1990 | Henry | 250/369 |
| 5,804,832 A | 9/1998 | Crowell et al. | 250/580 |
| 6,989,539 B2 | 1/2006 | Wischmann et al. | 250/370.11 |
| 7,170,973 B2 | 1/2007 | Gipp et al. | 378/98.8 |
| 7,183,556 B2 | 2/2007 | Yagi | 250/370.09 |
| 2003/0116716 A1 * | 6/2003 | Homme et al. | 250/370.11 |
| 2004/0178350 A1 * | 9/2004 | Nagano et al. | 250/370.11 |
| 2005/0062395 A1 * | 3/2005 | Takahashi et al. | 313/467 |

FOREIGN PATENT DOCUMENTS

| | | |
|---|---|---|
| JP | 09-145845 A | 6/1997 |
| JP | 2000-284053 A | 10/2000 |
| JP | 2001-504940 | 4/2001 |
| JP | 2004-033659 A | 2/2004 |
| JP | 2004-361879 A | 12/2004 |
| JP | 2005-524466 | 5/2005 |

OTHER PUBLICATIONS

Office Action dated Apr. 26, 2011, issued in Japanese counterpart application, No. 2007-000512 (partial translation provided above).

* cited by examiner

*Primary Examiner* — Constantine Hannaher
(74) *Attorney, Agent, or Firm* — Fitzpatrick, Cella, Harper & Scinto

(57) ABSTRACT

A radiation detection apparatus has a sensor panel including a photoelectric conversion unit with a plurality of photoelectric conversion elements over a substrate, a wavelength converter, disposed over the photoelectric conversion unit of the sensor panel, for converting a radiation into light detectable by the photoelectric conversion element, a plane shaped light emitting body for emitting light to the photoelectric conversion unit of the sensor panel, disposed over the wavelength converter, and a protective layer disposed on the plane shaped light emitting body.

11 Claims, 3 Drawing Sheets

RADIATION DETECTION APPARATUS AND RADIATION IMAGING SYSTEM

This application is a National Stage filing under 35 U.S.C. §371 of International Application No. PCT/JP2007/051208, filed Jan. 19, 2007.

TECHNICAL FIELD

The present invention relates to a scintillator panel, a radiation detection apparatus and radiation imaging system used in medical diagnosis apparatus, nondestructive inspection apparatus and others, and in particular, to a scintillator panel, a radiation detection apparatus and radiation imaging system used in X-ray radiographing.

BACKGROUND ART

An X-ray film system including a fluorescent screen provided with an X-ray phosphor layer therein and a double-faced coating material has been generally used for X-ray radiographing until now. A recent digital radiation detection apparatus with an X-ray phosphor layer and two-dimensional photodetectors has the following advantages and has been vigorously researched and developed. Applications for various patents thereon have been filed. That is to say, the digital radiation detection apparatus is superior in image characteristic and can share data with networked computers because it handles digital data.

Among other digital radiation detection apparatus, an apparatus disclosed in Japanese Patent Application Laid-Open No. 2000-284053 (patent family: U.S. Pat. No. 6,262,422, EP0903590 A1, and CN1501095(A)) is known as a highly sensitive and sharp apparatus. The apparatus forms a scintillator layer for converting radiation into light detectable on photodetectors. The photodetectors consist of a plurality of photosensors and photoelectric conversion units in which electric elements such as thin film transistors (TFT) serving as switching elements are two-dimensionally arranged.

Over a light receiving unit is formed a columnar crystal structured scintillator which is a wavelength converter for converting incident radiation into visible light and which consists of a columnar crystallized phosphor layer of alkali halide. A protective film is formed over the scintillator.

Incidentally, there are still the following problems to be solved in the photoelectric conversion unit: decreasing characteristic variation due to aging and S/N ratio reduction due to dark current, and shortening a photographing cycle to make the apparatus easy to use.

Emitting light before radiographing to decrease dark current permits one to provide an X-ray image high in S/N ratio in a short time. Thus, the emission of light to the photoelectric conversion unit by a light source is called "light reset," "bias light application" or "light calibration."

On the other hand, a conventional radiation detection apparatus disclosed in Japanese Patent Application Laid-Open No. 2004-33659 directly converts radiation into electric charge and is provided with a light source for applying light to an X-ray flat panel detector to suppress reduction in sensitivity of the detector.

However, the radiation detection apparatus including a wavelength converter to which the above light source is added is thickened, and thus is increased in size.

Furthermore, the addition of the composing element of the light source increases cost.

DISCLOSURE OF THE INVENTION

The present invention has for its purpose to provide a radiation detection apparatus which is compact in size, in spite of a light source emitting calibration light being added, and is lower in cost.

To solve the above problems the present invention provides a radiation detection apparatus comprising a sensor panel including a photoelectric conversion unit with a plurality of photoelectric conversion elements over a substrate, a wavelength converter, disposed over the photoelectric conversion unit of the sensor panel, for converting a radiation into light detectable by the photoelectric conversion element, a plane shaped light emitting body for emitting light to the photoelectric conversion unit of the sensor panel, disposed over the wavelength converter, and a protective layer disposed on the plane shaped light emitting body.

According to the present invention, the plane shaped light emitting body is interposed between the protective layer covering the wavelength converter and the sensor panel, which allows sharing parts of the composing elements of the protective layer and the light source.

For that reason, a small and low-cost radiation detection apparatus can be realized.

Further features of the present invention will become apparent from the following description of exemplary embodiments with reference to the attached drawings.

BEST MODE FOR CARRYING OUT THE INVENTION

The best mode for carrying out the present invention is described in detail below with reference to the drawings.

Figure 1:
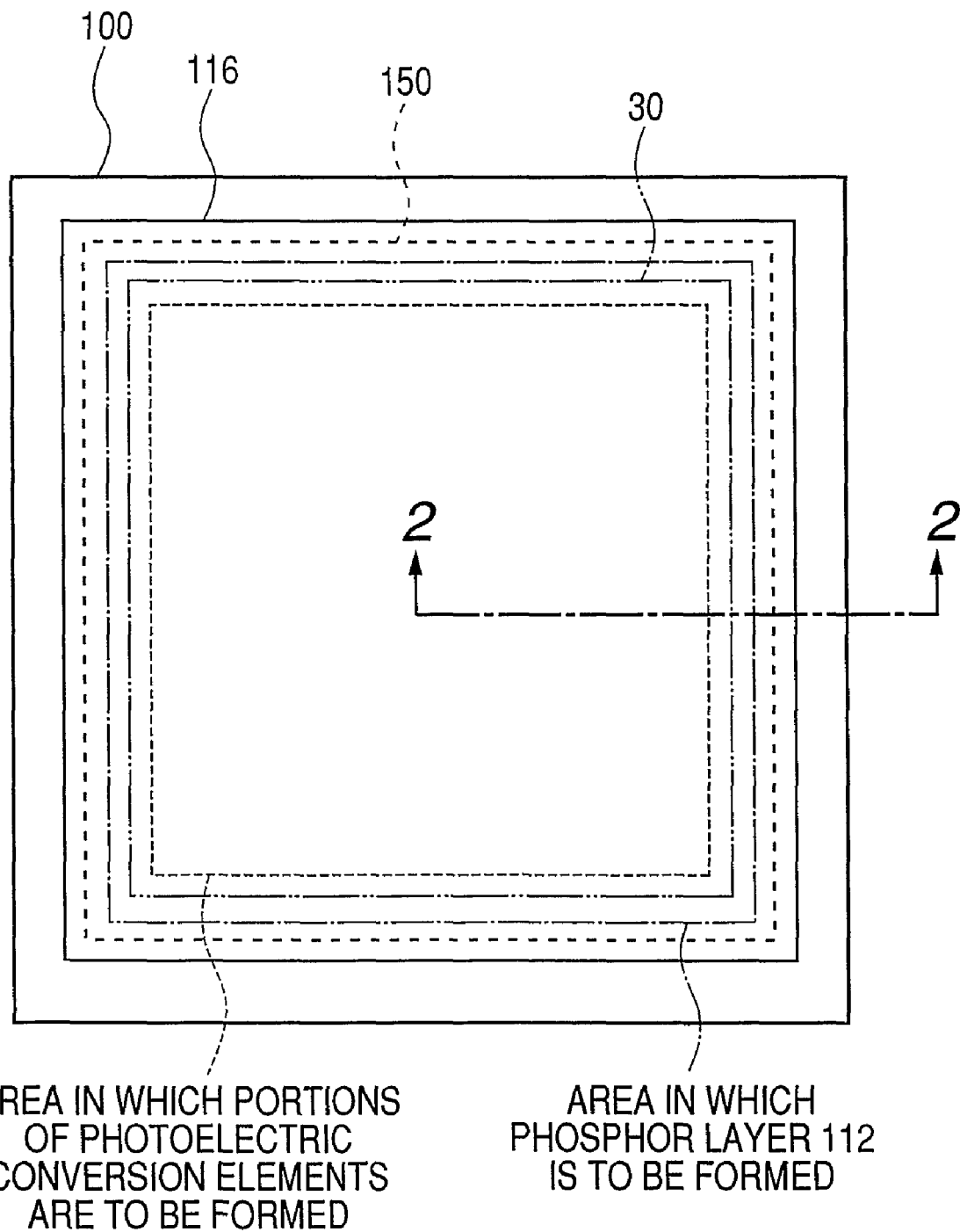
FIG. 1 is a schematic plan view showing a radiation detection apparatus according to a first embodiment of the present invention.
Figure 2:
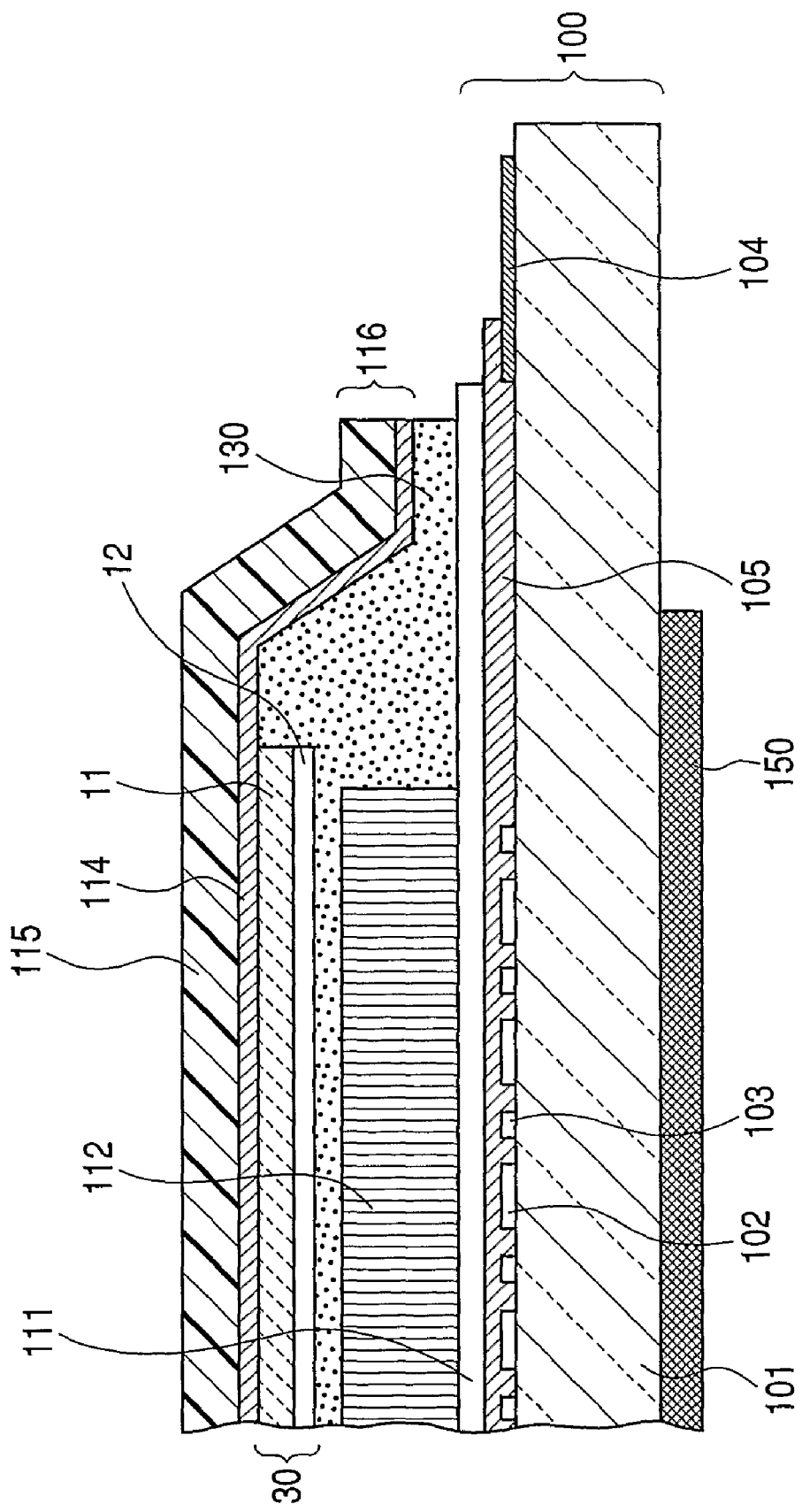
FIG. 2 is a schematic cross-section along line 2-2 in FIG. 1.

FIG. 1 is a general schematic plan view showing a radiation detection apparatus according to the embodiment of the present invention. FIG. 2 is a partial cross-section along line 2-2 in FIG. 1.

In FIG. 2, reference numeral 101 denotes a glass substrate that is an insulator; and 102, a photoelectric conversion element composed of a semiconductor photosensor using amorphous silicon and a TFT. Reference numeral 103 signifies a wiring; 104, a connecting lead; 105, a first protective layer consisting of silicon nitride and others; and 111, a phosphor underlying layer, formed by resin and others, serving also as a rigid protective layer of the photoelectric conversion elements. A sensor panel 100 is constituted by those components 101 to 111. Reference numeral 112 indicates a wavelength converter being a phosphor layer made of columnar phosphors. Reference numeral 116 represents a protective sheet being a protective layer covering the phosphor layer 112. Reference numeral 130 designates an adhesive layer that is a resin layer made of organic resin and the like. Reference numeral 114 denotes a reflection layer; and 115, a protecting base member. Reference numeral 150 represents a light absorption layer for absorbing light emitted by the wavelength converter and the light absorption layer is formed by bonding colored film sheets of PET by bonding material or adhesive.

As the protective layer 105 of the sensor panel used in the present invention, the following materials are used: polyphenylene sulfide resin, fluororesin, polyether ether ketone resin, liquid crystal polymer, polyether nitryl resin, polysulfone resin, polyether sulfone resin, polyarylate resin, polyamide-imide resin, polyetherimide resin, polyimide resin, epoxy resin, and silicone resin as well as SiN, $TiO_2$, LiF, $Al_2O_3$, and MgO. It is preferable that the protective layer in particular be high in transmissivity at the wavelength of light emitted by the phosphor because the protective layer transmits light converted by the phosphor at the time of applying radiation.

Any material may be used as the phosphor underlying layer 111, provided that it withstands the thermal processing (200° C. or higher) in the process of forming the phosphor layer using the columnar crystal structured phosphor. Materials include for example polyamide-imide resin, polyetherimide resin, polyimide resin, epoxy resin, silicone resin and others.

An alkali halide activator is preferably used as the phosphor layer 112. Such materials as CsI:Na, NaI:Tl, LiI:Eu, KI:Tl and others as well as CsI:Tl may be used. The phosphor layer 112 may be formed in such a manner that transparent resin, solvent, and additives as required such as dispersing agent and antifoaming agent are added to phosphor particles made of such phosphor materials as $CaWO_4$, $Gd_2O_2S$:Tb, $BaSO_4$:Pb and others, mixed with each other, and coated on the sensor panel 100. The phosphor layer formed by coating may be formed on the surface of a support made of resin and of the plane shaped light emitting body and thereafter fixed to the sensor panel 100 by adhesive layer to form the radiation detection apparatus.

Reference numeral 30 denotes a plane shaped light emitting body interposed between the phosphor layer 112 and the protective sheet 116 that efficiently emits calibration light to the photoelectric conversion element 102.

The plane shaped light emitting body 30 may be any light source selected from among those such as an EL light source and others usable in the backlight of a flat panel. In the present embodiment, a plane shaped light emitting light source, such as an EL light source and others, which is thin and can be formed in a sheet shape is preferably used. A light emitting region of the light source may be divided into a plurality of sub-regions if those emit light from the whole of them. Even though depicted in details, the plane shaped light emitting body 30 is desirably one provided with a protective member disposed at a side plane thereof. The protective member can thus reduce deficiency or malfunction of the light emitting layer due to shocks or moisture likely to be introduced therein from outside thereof.

The adhesive layer 130 is provided to fix the plane shaped light emitting body 30 and the protective sheet 116 over the sensor panel and aims at moisture-proof protection at peripheral ends of the protective sheet 116. Any material may be used for the adhesive layer 130, provided that it meets the purposes. A general sealing material of organic resin such as, for example, silicone, acryl, epoxy, polyester, polyolefin and others may be used, however it is desirable to use resin particularly low in moisture transmission.

It is desirable to use metal high in reflectivity such as Al, Ag, Cr, Cu, Ni, Ti, Mg, Rh, Pt and Au as material for the reflection layer 114 constituting the protective sheet 116. The protecting base member 115 is for forming the reflection layer 114 in advance and is preferably made of organic material of PET. The protective sheet 116 functions to perform a moisture-proof protection for the photoelectric conversion unit and the phosphor layer 112 formed on the sensor panel 100 and is preferably constituted by at least one layer made of a material low in moisture transmission.

The light absorption layer 150 is for absorbing light emitted from the phosphor layer 112 and incident on the insulating substrate 101 of the sensor panel. Since the light absorption layer 150 absorbs a light incident into the substrate of the sensor panel to reduce a reflected light and a scattered light introduced into a side of the photoelectric conversion unit, the resolution of the radiation detection apparatus can be improved.

The light absorption layer 150 is formed by bonding colored film sheets with adhesive or pressure sensitive adhesive (not shown). Materials for the film sheets usable for the light absorption layer 150 include PET, acryl, urethane, polyethylene, silicon, polyolefin, acrylonitrile butadiene, chloroprene and ethylene-propylene. In addition, a foam material with foams in the foregoing material may be used. Furthermore, a colored resin material such as acryl or the like may be directly coated on the sensor panel to form the layer. Any color may be used for coloring, provided that it absorbs the wavelength of light emitted by the phosphor layer.

The above description is concerned with the formation of the photoelectric conversion unit, as a sensor panel being a two-dimensional photodetector, consisting of photosensors using amorphous silicon and TFTs on the glass substrate. On the other hand, a radiation detection apparatus similar to the above may be constituted by arranging a backing layer and a phosphor layer over a semiconductor single crystal substrate on which image pick-up devices with two-dimensionally arranged CCDs or CMOS sensors are formed.

Embodiments on the radiation detection apparatus of the present invention are described below in detail.

First Embodiment

FIG. 1 is a general schematic plan view showing a radiation detection apparatus according to a first embodiment of the present invention and FIG. 2 is a partial cross-section along line 2-2 in FIG. 1.

As shown in FIG. 2, the photoelectric conversion element 102, or a photo detecting element (pixel) consisting of a semiconductor photo sensor made of amorphous silicon and a TFT and the wiring 103 are formed on the glass substrate 101 being an insulating substrate. On the upper part of that, the protective film (a first protective layer) 105 of $SiN_x$ and the phosphor underlying layer 111 of hardened polyimide resin are formed to constitute the sensor panel 100.

Over the sensor panel 100, the phosphor layer 112 is formed on the phosphor underlying layer 111 by a phosphor forming evaporation device to cover the area over the two-dimensionally arranged photoelectric conversion elements 102. The phosphor layer is made of columnar crystallized phosphors of alkali halide (for example, CsI:Tl, thallium activated cesium iodide).

The protective sheet 116 for protecting the phosphor layer 112 and the photoelectric conversion unit from moisture is a film sheet in which aluminum film is formed in advance as the reflection layer 114 on the 25 μm thick protecting base member 115 made of PET. The protective sheet 116 is arranged to cover the phosphor layer 112, the photoelectric conversion unit formed in the sensor panel 100 and the plane shaped light emitting body 30, and bonded and fixed to the sensor panel by the adhesive layer 130 on the periphery of the protective sheet.

The adhesive layer 130 is made of hot-melt type organic resin of polyolefin resin and enables adhesion and fixation by heating under pressure at a relatively lower temperature and in a shorter time.

The light absorption layer 150 is preferably arranged on the side opposite to the side where the phosphor layer 112 of the sensor panel 100 is formed. The reason is that the light absorption layer absorbs light from the phosphor layer to improve resolution. If a light absorption layer does not exist, light incident on the sensor panel reflects and scatters inside the substrate, and falls on the photoelectric conversion element 102 formed on the sensor panel 100. This causes the radiation detection apparatus to decrease in resolution, degrading image quality.

Furthermore, the light absorption layer 150 is preferably a 100 μm thick black PET sheet on which a pressure sensitive adhesive such as acrylic is coated in advance. It is preferable that the black PET sheet, which is a light absorption layer, be bonded and fixed to the sensor panel 100 with a roller-pressing device. Such a configuration simplifies the process to achieve a low cost.

In the present embodiment, an electroluminescence (EL) light source is used in the plane shaped light emitting body 30 interposed between the phosphor layer 112 and the protective sheet 116. The use of a thin plane-shaped light-emitting light source according to the present embodiment causes the phosphor layer to be close to the reflection layer, improving resolution.

The EL light source of the plane shaped light emitting body 30 is provided with an electrode for applying an alternate current voltage across both surfaces of the light emitting layer 11 made of phosphor dispersing in a binder high in dielectric constant. In the present embodiment, the EL light source is constituted by the reflection layer 114 made of aluminum in the protective sheet and used as one of electrodes or an upper electrode, the light emitting layer 11 coming in contact with the reflection layer 114 and a transparent light-emitting-layer lower-electrode 12 of ITO.

The reflection layer 114 constituting the protective sheet 116 according to the present embodiment functions to protect the upper electrode in the light emitting layer of light source of the plane shaped light emitting body, the phosphor layer and the photoelectric conversion element from moisture and to reflect light whose wavelength is converted by the phosphors back to the surface of the photoelectric conversion element.

The configuration described above in the present embodiment eliminates the need for providing another upper electrode for the light source, which allows reducing the number of the component elements of the radiation detection apparatus. This enables providing a small and low cost radiation detection apparatus.

Second Embodiment

An application of the radiation detection apparatus according to the present invention is described below.

Figure 3:
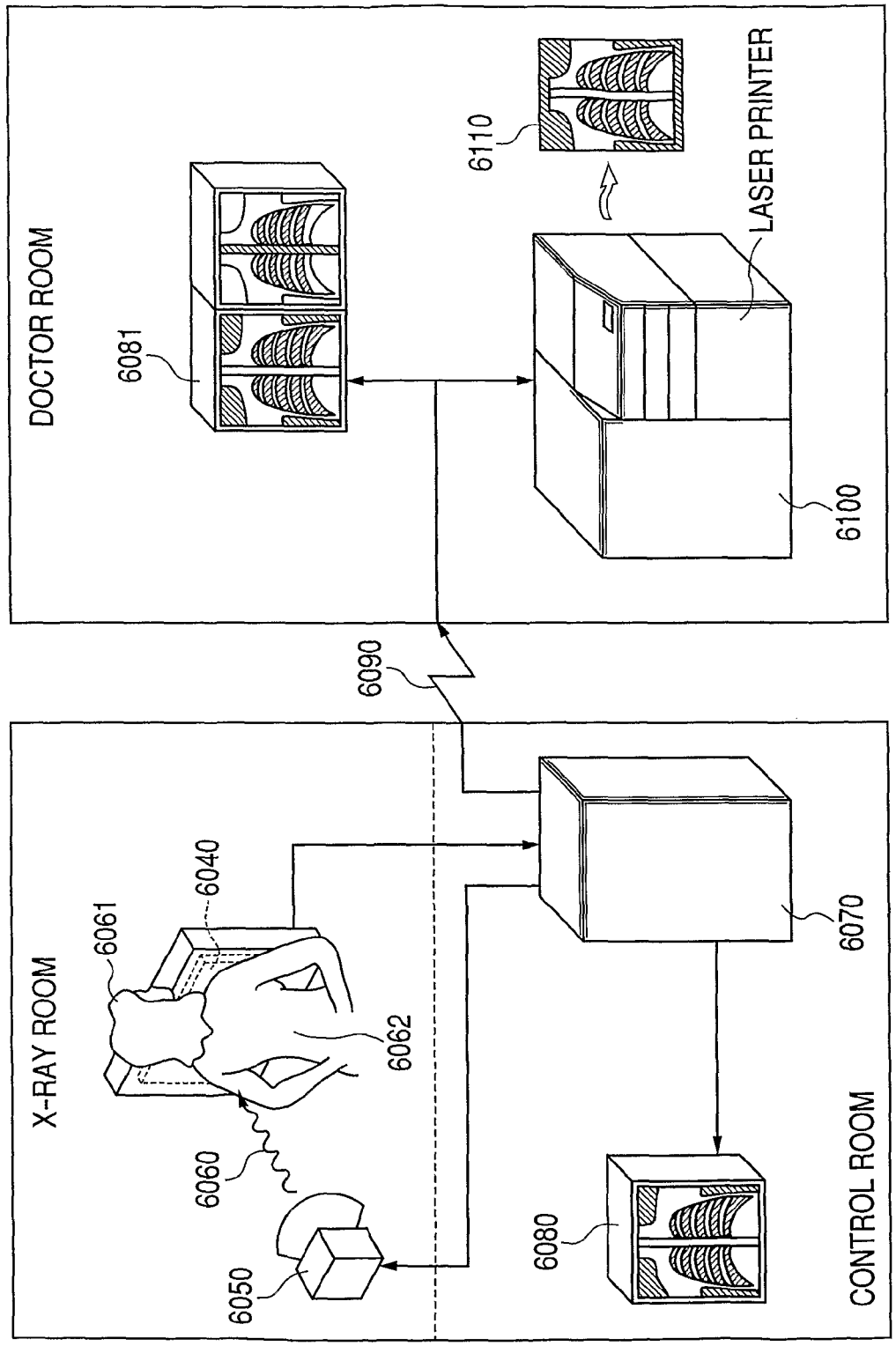
FIG. 3 is a schematic diagram showing the configuration of a radiation imaging system related to an application of the present invention.

FIG. 3 shows an application of the radiation detection apparatus according to the present invention to an X-ray diagnostic system as a radiation imaging system.

X-rays 6060 generated by an X-ray tube 6050 are transmitted through the chest 6062 of a patient or an examinee 6061 and are incident on a radiation detection apparatus 6040 on which scintillators (phosphors) are mounted. The incident X-rays include information on the body of the patient 6061. The scintillator emits light in response to the incidence of the X-rays and performs photoelectric conversion to provide electrical information. The information is converted into a digital signal, subjected to image processing by an image processor 6070, serving as signal processing means, and monitored by a display 6080, serving as display means, situated in a control room.

In addition, the information can be transferred to remote areas by transmission processing means such as a telephone network 6090 or the like, displayed by the display 6081, serving as display means, in a doctor's room at another location or stored in recording means such as an optical disk. This allows a doctor in a remote area to make a diagnosis. Furthermore, the information can be recorded in a film 6110, serving as a recording medium, by a film processor, serving as being recording means.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-016396, filed Jan. 25, 2006, and Japanese Patent Application No. 2007-000512, filed Jan. 5, 2007, which are hereby incorporated by reference herein in their entirety.

The invention claimed is:

1. A radiation detection apparatus comprising:
a sensor panel including a photoelectric conversion unit provided with a plurality of photoelectric conversion elements;
a wavelength converter, disposed over the photoelectric conversion unit, for converting radiation into light detectable by the photoelectric conversion elements;
a protective layer covering the wavelength converter, and having a base member and a metal layer disposed between the wavelength converter and the base member;
an electroluminescence light source, having a light-emitting layer disposed between electrodes for applying an alternating current voltage across the light-emitting layer, for emitting light to the photoelectric conversion unit, wherein the electroluminescence light source is disposed between the wavelength converter and the base member, one of the electrodes is a light-transmitting electrode disposed between the wavelength converter and the light-emitting layer, and the other of the electrodes is the metal layer and functions to reflect the light converted by the wavelength converter to the photoelectric conversion elements and to emit light from the light-emitting layer to the photoelectric conversion elements; and
an adhesive layer disposed between the light-transmitting electrode and the wavelength converter and disposed between the protective layer and the sensor panel, wherein the electroluminescence light source is bonded and fixed to the wavelength converter by the adhesive layer, and the protective layer is bonded and fixed to the sensor panel at the periphery of the protective layer.

2. The radiation detection apparatus according to claim 1, further comprising a light-absorption layer disposed on a side opposite to a side where the electroluminescence light source is disposed.

3. The radiation detection apparatus according to claim 2, wherein a first area where the light-emitting layer is disposed is larger than a second area where the plurality of photoelectric conversion elements are disposed, and the first area is smaller than a third area where the protective layer is disposed.

4. The radiation detection apparatus according to claim 3, wherein the electroluminescence light source is bonded and fixed to the wavelength converter by the adhesive layer at the first area, and the protective layer is bonded and fixed to the sensor panel at the periphery of the protective layer in the third area.

5. The radiation detection apparatus according to claim 3, wherein a fourth area where the light absorption layer is disposed is larger than the first area, and the fourth area is smaller than the third area.

6. The radiation detection apparatus according to claim 3, wherein the sensor panel further includes a phosphor underlying layer covered covering the plurality of photoelectric conversion elements, and a fifth area where the phosphor underlying layer is larger than the third area.

7. A radiation imaging system comprising:
a radiation detection apparatus according to claim 1;
signal processing means which processes a signal from the radiation detection apparatus;
recording means which records a signal from the signal processing means;
display means which displays a signal from the signal processing means;
transmission processing means which transmits a signal from the signal processing means; and
a radiation source which generates the radiation.

8. The radiation detection apparatus according to claim 1, wherein the adhesive layer is formed from a hot melt resin.

9. The radiation detection apparatus according to claim 1, wherein the wavelength converter comprises a plurality of columnar crystals.

10. The radiation detection apparatus according to claim 1, wherein the base member is made of organic material.

11. The radiation detection apparatus according to claim 1, wherein the metal layer reflects the light converted by the wavelength converter through the light-emitting layer and the light-transmitting electrode to the photoelectric conversion elements.

* * * * *